United States Patent [19]

Marquez Perez et al.

[11] Patent Number: 4,623,648

[45] Date of Patent: Nov. 18, 1986

[54] 1-AZAXANTHONE FOR USE AS THERAPEUTIC AGENT AS AN ANTIPYRETIC, ANALGESIC, ANTI-INFLAMMATORY AND BRONCHODILATOR

[75] Inventors: Miquel Marquez Perez; Ricardo Matas Docampo; José M. Puigmarti Codina; José Repolles-Moliner; Jorge Serra Sola, all of Barcelona, Spain

[73] Assignee: Lacer, S.A., Barcelona, Spain

[21] Appl. No.: 668,179

[22] Filed: Nov. 5, 1984

Related U.S. Application Data

[63] Continuation of Ser. No. 420,092, Sep. 20, 1982, abandoned.

[30] Foreign Application Priority Data

Sep. 25, 1981 [EP]  European Pat. Off. ........ 81107651.2

[51] Int. Cl.$^4$ ................ A61K 31/435; C07D 491/147
[52] U.S. Cl. ........................................ 514/291; 546/89
[58] Field of Search ........................... 514/291; 546/89

[56] References Cited

U.S. PATENT DOCUMENTS 3,803,153  4/1974  Villani ................................. 546/89

OTHER PUBLICATIONS

Nantka-Namirski I, Chem. Abstracts, vol. 82, (9), Abst. No. 57, 664s, Mar. 3, 1975.
Nantka-Namirski II, Chem. Abstracts, vol. 88, (7), Abst. No. 50, 686r, Feb. 13, 1978.

*Primary Examiner*—Alan L. Rotman
*Attorney, Agent, or Firm*—Oblon, Fisher, Spivak, McClelland & Maier

[57] ABSTRACT

Ring closure methods for the preparation of 1-azaxanthone and the use of the compound as therapeutic agent.

9 Claims, No Drawings

1-AZAXANTHONE FOR USE AS THERAPEUTIC AGENT AS AN ANTIPYRETIC, ANALGESIC, ANTI-INFLAMMATORY AND BRONCHODILATOR

CROSS-REFERENCE

This application is a continuation of Ser. No. 06/420,092, filed Sept. 20, 1982, now abandoned.

This invention relates to the production of 1-azaxanthone and the use of the compound in the treatment of various mammalian diseases. It relates also to pharmaceutical compositions containing this compound including such compositions in dosage unit forms.

The compound 1-azaxanthone is represented by the formula:

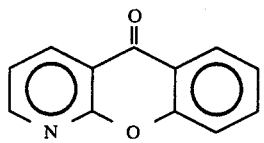

It is a known chemical compound the first synthesis of which was reported by F. G. Mann and J. H. Turnbull (J. Chem. Soc. 1951, 761-2). It has not previously been described as having any pharmaceutical activity. F. G. Mann, J. A. Reid, J. Chem. Soc. 1952, 2057-62 carried out investigations about a possible use as schistosomicide but found that 1-azaxanthone did not show any "significant effect on schistosomiasis infections". 1-azaxanthone has been used as an intermediate for the production of other compounds, especially 1-azaxanthone derivatives some of which had shown pharmaceutical properties, e.g. as antiallergics, bronchodilators, antiinflammatories or analeptics. The properties of these compounds depended on the various side chains introduced into the 1-azaxanthone molecule.

It was now found that 1-azaxanthone has surprising and valuable therapeutical properties on various fields of human and veterinary therapy.

Thus, it has shown activity in standard and well-recognized animal models as analgesic, antipyretic, antiinflammatory, spasmolytic, bronchodilatory, antibronchoconstrictor and diuretic agent. Accordingly, it is useful in the preventive or curative treatment of those animal or human symptomatic and pathological processes related with these pharmacological activities.

Representative examples of pharmacological and toxicological results obtained in various standard tests are described in detail below.

Pharmacological results

Sprague-Dawley rats, Swiss mice, California rabbits and mongrel guinea pigs and cats were used. 1-azaxanthone was administered as a suspension in 0.5 % w/v of carboxymethyl-cellulose in distilled water for oral and i.p. administration. When administered i.v. or to the nutrient liquid of the isolated tissues, a solution of the compound in isopropylidenglycerol (15 mg/ml) was used.

Analgesic activity

Acetic acid induced writhing in mice (according to R. Koster et al., Fedn. Proc. 1959, 18, 412). In this test, 1-azaxanthone had an $ED_{50}$ of 2.8 mg/kg (2.1–3.4, 95% confidence limits) by oral route.

Phenyl-p-benzoquinone induced writhing in mice (according to E. A. Siegmund et al., J. Pharmacol. Exptl. Therap. 1957, 119, 453). The compound had an $ED_{50}$ of 8.9 mg/kg (6.1–11.8, 95% confidence limits) by oral route. I Hyperalgesia in rat inflamed paw (according to L. O. Randall and J. J. Selitto, Arch. Int. Pharmacodyn. 1957, 111, 409). 1-azaxanthone showed an $AID_2 = 18.4$ mg/kg per os ($AID_2$ being defined as the dose that increases twice the analgesic threshold of the control animals).

Hot plate test in mice. An analgesimeter LETICA model 7000 was used, the temperature of the plate being maintained at 57°±0.5° C. The test compound was administered by oral route 1 hour before placing the animals on the plate. The $ED_{50}$ was 21 mg/kg (11–39, 95% confidence limits).

"D'Amour and Smith" test in rats (see J. Pharmacol. Exptl. Therap., 1941, 72, 74). An analgesimeter LETICA model 7100 was used. An oral dose of ca. 100 mg/kg of 1-azaxanthone, administered 1 hour before testing produced analgesia in 50% of the animals.

Antipyretic activity

Yeast-induced hyperthermia in rats (according to U. M. Teotino et al., J. Med. Chem. 1963, 6, 248). The test compound was administered by oral route 1 hour before the s.c. injection of the pyrogenic agent. Under these conditions a dose of 6.2 mg/kg of 1-azaxanthone completely prevented the hyperthermia in the treated animals 4 hours after the yeast injection (when the increase in rectal temperature of the control group was 1.8° C.), and 6 hours after the yeast injection the same dose produced a decrease of 0.8° C. with respect to the 1.4° C. total increase in control animals. 1-azaxanthone also showed a statistically significant antipyretic effect (2nd and 3rd hours) at a dose as low as 0.375 mg/kg.

Hyperthermia induced in rabbits by i.v. injection of lipopolysaccharide of Escherichia coli (according to C. A. Winter and G. W. Nuss, Toxic. Appl. Pharmacol. 1963, 5, 247). In this test 1-azaxanthone by i.p. route was effective in preventing the increase in rectal temperature in rabbits having received an injection of 0.1 µg/kg of lipopolysaccharide; a dose of 200 mg/kg completely protected the animals, and a dose of 100 mg/kg reduced the 1.85° C. increase of the control animals (5 animals per group) by 0.7° C. The compound was also effective when administered to rabbits with established fever; for example, when 200 mg/kg of 1-azaxanthone were administered i.p. to a group of 5 rabbits from a total of 10 with mean hyperpyrexia of +1.15° C. 2 hours after the lipopolysaccharide injection, the hyperpyrexia of the treated group was +0.7° C. at 2 hours and +0.1° C. at 3 hours, while the hyperpyrexia of the untreated animals was 1.5° C. at 2 hours and 1.15° C. at 3 hours (all periods after administration of the test compound).

Antiinflammatory activity

Carrageenan rat paw oedema (according to C. A. Winter et al., Proc. Soc. Exptl. Biol. N.Y. 1962, 111, 544). 1-azaxanthone had an $ED_{50}$ of 21.7 mg/kg per os (6.0–37.3, 95% confidence limits). Activity was also found in this test with bilaterally suprarenalectomized rats (39% inhibition at 200 mg/kg per os).

Cotton-pellet granuloma (according to R. Meier et al., Experientia (Basel), 1950, 6, 469). 1-azaxanthone, administered at 200 mg/kg/day per os during 5 consecutive days inhibited the weight of dried granuloma tissue by 17.4% and that of wet tissue by 13.5%.

Carrageenan-induced abscess (according to K. F. Benitz and L. M. Hall, Arch. Int. Pharmacodyn. 1963, 144, 185). The test compound, administered at 50×2 mg/kg per os inhibited the dry weight of the formed abscess by 48.4% and the wet weight of it by 34.6%.

1-azaxanthone showed activity also in the following tests: turpentine-induced pleurisy, granuloma pouch, Evans blue permeability assay and Mycob. Butyricum induced arthritis (only in preventative treatment).

Spasmolytic activity

Guinea pig ileum (according to R. Magnus, Pflugers Arch. Ges. Physiol. 1904, 102, 123). In this "in vitro" assay 1-azaxanthone had the following $ED_{50}$ with different agonists (dose which inhibits the response of the ileum to the agonists by 50%):

| Agonists | $ED_{50}$ (µg/ml) |
| --- | --- |
| Acetylcholine | 14.26 |
| Histamine | 22.88 |
| Nicotine | 27.80 |
| $BaCl_2$ | 19.73 |

Charcoal intestinal transit in mice. 1-azaxanthone was administered i.p. 1 hour before the oral administration of 0.1 ml/mouse of an active charcoal suspension (10 g of charcoal and 1 g of gum arabicum +70 ml of distilled water). 1.5 hours after the charcoal administration the animals were sacrificed, and the length travelled by the charcoal from the pylorus was measured. The compound inhibited the charcoal intestinal transit by 37% at 12.5 mg/kg, 22% at 6.2 mg/kg and 15% at 4 mg/kg. Lower doses were inactive.

1-azaxanthone administered endovenously (4 mg/kg) also inhibited physiologic peristaltic movements in cats, measured by a balloon located intraluminally in the small intestine and connected to a pressure transducer (model H.P. 270).

Bronchodilator and antibronchoconstrictor activities

Isolated guinea pig tracheal chain (according to J. C. Castillo and E. K. DeBeer, J. Pharmacol. Exptl. Ther. 1947, 90, 104). 1-azaxanthone produced maximum relaxation of the tracheal muscle at a concentration of 20 µg/ml in the bath nutrient liquid. The minimun effective dose was about 5 µg/ml.

Inhibition of the bronchoconstrictor response to histamine in guinea pig (according to H. Konzett and R. Rossler, Arch. Exptl. Path. Pharmak. 1940, 195, 71). 1-azaxanthone (8 mg/kg i.v.) inhibited the response induced by 5 µg of histamine by 100% at 5 min, 67% at 10 min, 50% at 20 min, and 15% at 30 min after administration.

Inhibition of the bronchoconstrictor response to bradykinin in guinea pig (according to H. Konzett and R. Rossler, ibid.). 1-azaxanthone (8 mg/kg i.v.) produced a 100% inhibition of the response induced by bradykinin when the test compound was administered 10 min after 6 µg and 8 min before 12 µg of bradykinin.

Diuretic activity 1-azaxanthone was administered orally to rats (groups of 10) in a volume of 5 ml/rat immediately before allocating the animals to metabolism cages. The total volume of urine was measured 6 and 24 hours later. 10 mg/kg of 1-azaxanthone increased the total volume with respect to the control group by 94% in the first 6 hours and 44% in the 24 hours period. Sodium excretion was also increased.

Toxicological studies

The acute toxicity of 1-azaxanthone was evaluated in rats and mice. $LD_{50}$ values ranged between 400-600 mg/kg (i.p. route) and between 600-2000 mg/kg (oral route) depending on species and sex. For example, $LD_{50}$ (i.p. female rats) was 420 mg/kg; $LD_{50}$ (i.p. female mice) was 600 mg/kg; $LD_{50}$ (orally, male rats) was $\approx 2$ g/kg.

Gastric and rectal mucosae of rats tolerated the compound well, and the liver eliminated sulphobromophthalein well after a dose of 200 mg/kg/day by oral route during 14 consecutive days.

In a subacute toxicity study in rats (42 consecutive days, oral route) 1-azaxanthone did not show any drug-related toxic effect, even at the highest dose used (200 mg/kg/day). The treated animals developed a hepatomegaly which showed histologically as increased volume of hepatic nucleoles, and which can be explained as reaction of the hepatocytes, through activated protein synthesis, to the increased metabolic needs; in another study this hepatomegaly was seen to be fully reversible when discontinuing the administration.

In chronic adminstration to rats (92 consecutive days, oral route) a dose of 25 mg/kg/day was without statistically significant effect on the body weight increase and on the following parameters: number of erythrocytes, number of leucocytes and white cell distribution, serum Na, K and chlorides, total proteins, total lipids, cholesterine, uric acid, urea, glucose, GPT and GOT transaminases, alkaline phosphatases, hemoglobin, hematocrit and E.S.R. The weights of the main organs (liver, spleen, kidney, sexual glands, thymus, suprarenal glands, thyroid, lung, heart) were within normal limits. Only at 100 mg/kg/day some of these parameters were altered when compared to those of the control group, but all animals survived.

In a 6 months toxicity evaluation (25, 50 and 100 mg/kg/day, p.o.) in rats the results were almost the same as in the 92 days study.

Some preliminary teratogenesis studies in rats did not show any clear specific teratogenic potential.

The drug has no effect on the cardiocirculatory system (rats, cats and dogs). Clear activity on the central nervous system was not observed, and only some signs of depression were noted in mice and rats at high doses.

1-azaxanthone may be formulated into pharmaceutical compositions for its convenient use in human or veterinary therapy.

The invention therefore includes within its scope pharmaceutical compositions containing 1-azaxanthone as active ingredient, formulated with pharmaceutically acceptable carriers. These compositions may be, for instance, solid or liquid preparations for oral administration, such as tablets (coated or uncoated), capsules, powders, granules, pills, suspensions or emulsions; suppositories for rectal administration; creams, ointments or aerosols intended for topical administration; liquid or suspension sterile formulations for use by injection. Illustrative examples of some compositions and methods of their preparation will follow.

In any pharmaceutical preparation in which 1-azaxanthone is in solid state, such as tablets, capsules or suspensions for oral administration, supositories formulated with non-miscible bases, aerosols of the suspension/dispersion system, non-solubilized drug semisolids (pastes, creams) for topical application, the particle size of the active drug is one important factor affecting absorption and the corresponding onset of activity due to some physico-chemical properties of 1-azaxanthone, such as its low water solubility. Usually mean particle sizes of less than loo microns are used.

The effective dose of 1-azaxanthone will mainly depend on the disease or symptom to be treated and on the route of administration, and will accordingly vary within a fairly broad range, but generally it is in the range of 1 mg/kg/day and 50 mg/kg/day. Suitable dosage units are, for example, those within a range of 50 mg to 1000 mg. A desired daily dose can be achieved by administering a fraction or a multiple of the particular dosage unit used in accordance with standard procedures well understood by physicians and veterinarians.

It is to be understood that the mentioned dose range is only given as reference, because the effective dose for each patient (animal or human) depends on many factors, i.e. not only the specific activity desired or route of administration but also age, sex, body weight, excretory organs functionality, co-administration with other drugs or individual metabolic pattern.

Production of 1-azaxanthone 1-azaxanthone has been obtained by cyclization of 2-phenoxynicotinic acid with phosphorous oxychloride or polyphosphoric acid. 2-phenoxynicotinic acid in turn is produced by reacting 2-chloronicotinic acid with sodium phenoxide.

In the cyclization step, the use of phosphorous oxychloride (F. G. Mann et al., J. Chem. Soc. 1951, 761-2; ibid. 1952, 2057-62) gave unsatisfactory results which were later improved using polyphosphoric acid as a dehydrating agent, usually in very great excess (F. G. Villani et al., J. Med. Chem. 1975, 18, 1-8; Chem. Abstr. 86, 55315; Chem. Abstr. 88, 50686). The reaction was carried out by heating a mixture of 2-phenoxynicotinic acid and polyphosphoric acid at temperatures which ranged from 100°-120° C. to 160° C., diluting the cooled reaction mixture with water, and fully neutralizing with concentrated NaOH the highly acidic solution or suspension obtained. The crude solid formed was usually recrystallized (from benzene or ethanol) and in some cases a sublimation "in vacuo" was combined with the crystallization step. The melting point reported varies from 178°-182° C. to 182-183° C.

The use of polyphosphoric acid in a proportion to 2-phenoxynicotinic acid as high as 50:1 by weight requires the use of large amounts of aqueous NaOH to neutralize the excess inorganic acid, and great volumes of water must be handled. Also, the full neutralization of the aqueous solution or suspension obtained after the reaction produces large amounts of sodium phosphates which partly co-precipitate with 1-azaxanthone and are difficult to eliminate. If polyphosphoric acid is used in lesser proportion, a very thick and heterogeneous paste is formed with the organic acid, as in these reported procedures both products are mixed before heating. This mixture is very difficult to homogenize and to heat properly, and, as this cyclization reaction is exothermic, it usually reacts suddenly in an uncontrollable manner.

For obtaining the intermediate 2-phenoxynicotinic acid 2-chloronicotinic acid was reacted with an excess of phenol in methanol or ethanol to which metallic sodium or sodium methoxide had been added in stoichiometric quantity (stoichiometric in relation to the carboxylic acid and the phenol). The alcohol was removed by distillation, the residue was heated to 170°-180° C. for 1 to 5 hours, cooled and poured into ice or water, the solution was extracted several times with ethyl ether, acidified and filtered. After washing with water the product was dried and recrystallized.

In this reaction the use of phenol in great excess requires several extractions of the aqueous solution with an organic solvent, as the phenol is not fully removed from the melted mass in the actual reaction step even at high temperatures.

Generally, this known overall process with reported working conditions—although suited for laboratory scale and for obtaining a product to be used as intermediate—has proved to be inconvenient for large batches or for industrial production due to the large number and complexity of operations steps involved, and the dangerous and uncontrollable cyclization step. In particular, it proved to be unsuitable for obtaining very pure 1-azaxanthone for use in the pharmacotherapeutic field in satisfactory and reproducible yields.

The improved process of the invention for obtaining 1-azaxanthone avoids these disadvantages and makes possible the production of 1-azaxanthone of high purity suitable for the claimed new use and with good yield. The specific working conditions in the new process, assure easy control of the exothermic cyclization reaction and avoids the lengthy, cumbersome and costly operations previously employed.

The two-step process for producing pure 1-azaxanthone starts from 2-chloronicotinic acid which is reacted with sodium phenoxide at 160°-200° C., the mixture is dissolved in water and acidified, the 2-phenoxynicotinic acid obtained is cyclized with a dehydrating agent, usually polyphosphoric acid, at 120°-200° C. The cooled mixture is dissolved in water and neutralized with an alkaline hydroxide, and the precipitated 1-azaxanthone is washed and recrystallized.

According to the invention, 2-chloronicotinic acid in alkaline metal salt form is reacted with alkaline metal phenoxide without an excess of phenol at 160°-200° C. The molten mass is partly cooled, water is added until complete solubilization, the aqueous solution is acidified and the solid obtained is dried. In the cyclization step the thus obtained 2-phenoxynicotinic acid is added portionwise to 5-10 times its weight of polyphosphoric acid which has been previously heated, the temperature is raised to 160°-200° C., the reaction mixture is cooled and diluted with water. Concentrated aqueous alkali hydroxide is added to adjust the pH to 2-3, the solid is filtered, washed, dried and recrystallized, obtaining very pure 1-azaxanthone in an overall yield of 50-70%.

Alternatively, in another way of carrying out this process, the crude reaction mixture containing the alkali metal salt of 2-phenoxynicotinic acid is used as such in the cyclization step, without isolating the 2-phenoxynicotinic acid. The polyphosphoric acid used must have a $P_2O_5$ content of 80-85%, because lower contents of $P_2O_5$ adversely affect the dehydration reaction.

1-azaxanthone can also be obtained by reacting a compound of formula (II):

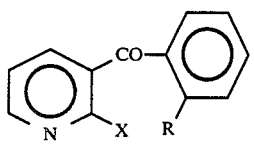

wherein X is Cl, Br or alkoxy containing from one to four carbon atoms, and R is halogen, preferably F, OH or alkoxy containing one to four carbon atoms, with concentrated hydrochloric or hydrobromic acid, usually at reflux temperature of the mixture, and isolating the desired product after removing the excess inorganic acid by distillation or neutralization with an alkali.

The intermediates of formula II (X=Cl, Br) can be obtained by oxidizing a 3-(2-R-benzoyl)-pyridine with $H_2O_2$: acetic acid, reacting the 3-(2-R-benzoyl)-pyridine-N-oxide so obtained with halogenating agents, such as $POCl_3$, $POBr_3$ or $PCl_5$, and isolating the desired compound of formula II (X =Cl, Br). Compounds of formula II (X=$C_{1-4}$ alkoxy) are easily obtained by reacting a compound of formula II (X=Cl, Br) with an alkali metal alkoxide. Compounds of formula II, in which X is Cl or Br, and R is OH, can be obtained by Fries-rearrangement of phenyl-2-chloronicotinate or phenyl-2-bromonicotinate.

The following non-limiting examples are given by way of illustration only.

EXAMPLE 1

(a) 55.2 g of sodium was added portionwise to 1500 ml of anhydrous methanol. When the reaction was complete 120 g of phenol and 200 g of 2-chloronicotinic acid were added, and the mixture was heated until completely solubilized. The methanol was removed by distillation, and the residue heated to 180°-200° C. for 5 minutes. The molten mass was cooled to about 100° C., and water was added slowly. The solution obtained was acidified with hydrochloric acid. After standing for about 16 hours, the solid obtained was filtered and dried, giving 237.4 g of 2-phenoxynicotinic acid, as white crystals, m.p. 179-181° C. (Kofler micro hot-stage); neutralization equivalent: 215.20 (calculated 216.55).

(b) 1410 g of polyphosphoric acid (85% of $P_2O_5$) was heated in an open flask to 150°-160° C. Then 235 g of 2-phenoxynicotinic acid was added slowly in small portions. The mixture was heated to 160°-180° C. for 30 minutes, cooled to 100° C. and poured into ice:water. To the suspension obtained, 10 N NaOH was added slowly to adjust the pH to 2. After standing in the refrigerator, the solid which formed was filtered, suspended in water and diluted NaOH was added to neutralize. The crystalline solid was filtered, washed well with water and dried. There was obtained 181 g of crude product, which was recrystallized and decolorized from ethanol, affording 157.8 g of pure 1-azaxanthone, as white needles, m.p. 184°-185° C. (Kofler micro hot-stage); and m.p. 184.5°±0.2° C. when a Mettler/FP-61 capillary melting point apparatus was used at a temperature increase rate of 1° C./min. With this apparatus and the same heating rate the melting point of 1-azaxanthone from several similarly prepared batches was between 184.3° and 185.3° C., while an analytical standard (recrystallized twice from ethanol and vacuum sublimed) had a m.p. of 185.4°±0.2° C.

The product obtained by the above method was chromatographically pure, using either chloroform (Rf: 0.15), ethyl acetate (Rf: 0.76), chloroform/ethyl acetate 10/1 (Rf: 0.46)or ethylacetate/methanol 3/1 (Rf: 0.73) in silica gel chromatoplates Merck 60 F 254 (unactivated). It showed a content greater than 99.4% by UV spectrophotometry (in ethanol or water) or by high pressure liquid chromatography, using as standard the analytical grade 1-azaxanthone just mentioned, which had absorption maxima at 335 nm ($\epsilon$=6,425), 282 nm ($\epsilon$=10,210) in ethanol; and 335 nm ($\epsilon$=6,330), 286 nm ($\epsilon$=11,430) in water.

The solubilities of 1-azaxanthone in several solvents were determined at 20-25° C. by the equilibrium (saturation) technique, measuring the concentration spectrophotometrically at 335 nm or by high pressure liquid chromatography/spectrophotometry. The following values (in mg/ml) were obtained: water: 0.08; 0.1 N HCl: 0.07; 0.1 N NaOH: 0.07; buffer pH 7.4: 0.06; methanol: 7.6; ethanol: 6.2; propyleneglycol: 5.0; ethyl acetate: 20; chloroform: >50; dioxane: 65.

EXAMPLE 2

56.4 g of phenol and 100 g of 2-chloronicotinic acid were added to a solution obtained from 27.6 g of sodium and 800 ml of anhydrous methanol. After stirring for 30 minutes, the solvent was distilled off. The residual solid was melted (180°-190° C.) and the molten mass well homogenized during 5-10 minutes. After cooling, the solid was mixed with 700 g of 85% polyphosphoric acid and, following work up as in example 1, there was obtained 58.5 g of 1-azaxanthone, m.p. 184.6°±0.2° C. (Mettler FP-61; 1° C./min).

EXAMPLE 3

(a) 17 g of (2-methoxyphenyl)-(3-pyridyl)-methanone, b.p. 123°-135° C./0.5 mm Hg, 60 ml of glacial acetic acid and 30 ml of 30% $H_2O_2$ were heated to 60° C. for 1 hour. The solvents were vacuum distilled in a rotary evaporator and the residue extracted with chloroform. After removing the solvent there was obtained a yellow oil which slowly crystallized, affording about 16 g of the N-oxide, m.p. 105°-113° C., soluble in ethanol, acetone and chloroform and insoluble in water.

(b) 15 g of this N-oxide and 100 ml of phosphorous oxychloride were refluxed for 2 hours. The excess $POCl_3$ was distilled off and the crude oil added to water:ice. The acidity was partly neutralized with NaOH, and the solution was extracted with dichloromethane. The organic layer, washed with water, was dried, and the crude was chromatographed on a silica column, eluting with ethyl ether: petroleum ether 1:1. From the first fraction there was obtained 2.3 g of 6-chloro-3-(2-methoxybenzoyl)-pyridine, m.p. 46°-47° C., and from the second one 4.2 g of 2-chloro-3-(2-methoxybenzoyl)-pyridine, as a yellowish oil; Cl found: 14.02% (theory: 14.32%).

(c) 50 mg of the thus obtained 2-chloro-3-(2-methoxybenzoyl)-pyridine and 1 ml of 47% aqueous HBr were refluxed for 4 hours. The reaction liquid was added to water, neutralized with dilute NaOH, and the solid obtained filtered and dried, affording 20 mg of a product which is identical to the 1-azaxanthone obtained in Examples 1 and 2.

EXAMPLE 4

Production of pharmaceutical compositions containing 1-azaxanthone (a) Due to the good compressibility properties of 1-azaxanthone, tablets with low contents of additives can be obtained. A typical composition is as follows:

| | |
|---|---|
| 1-azaxanthone | 200 mg |
| Avicel PH-102 | 20 mg |
| Ac-Di-Sol | 2 mg |
| Mg stearate | 2 mg |
| Aerosil 200 | 1 mg |

Avicel PH-102 is a brand of microcrystalline cellulose with a mean particle size of 90 μm. Ac-Di-Sol is a registered trademark for sodium carboxymethyl cellulose (crosslinked). Aerosil 200 is a brand of colloidal silica with a specific surface of 200 m²/g.

For preparing 6,000 tablets of said composition 12 g of Ac-Di-Sol, 12 g of Mg stearate and 6 g of Aerosil 200 (sieved through 40 mesh U.S. Standard) are premixed in a mortar and blended for 1 minute in a cubic Erweka mixer. Then 120 g of Avicel PH-102 and 1200 g of 1-azaxanthone (90–95% with a mean particle size of 15–30 μm) are added, mixed for 30 minutes, and the powder obtained is compressed in an excentric tableting press using 10 mm diameter punches. The tablets are dry granulated in a Frewitt oscillator apparatus and passed through 18 mesh U.S. Standard. The so obtained granule is finally compressed with 8 mm punches to obtain tablets each weighing 0.225 g and which show a good disintegration time.

(b) For preparing about 5,000 rectal suppositories each containing 400 mg of 1-azaxanthone, 250 g of Tween 80 and 125 g of Aerosil 200 are added with good stirring to a molten mass of 10,625 g of Supol IA-15 at a temperature not higher than 50° C. (Tween and Supol are registered trademarks for polyoxyethylene sorbitan esters and a mixture of mono-, di- and triglycerides resp). When the Aerosil is well dispersed 2000 g of 1-azaxanthone is added, and the suspension is slightly cooled to 40° C. and molded in an automatic rotary Crespi machine, using molds of a size adequate to provide suppositories with an average weight of 2.6 g. All solid substances used were previously sieved through 40 mesh U.S. Standard.

(c) A suspension for oral use is prepared according to the following formula:

| | |
|---|---|
| 1-azaxanthone | 20 g |
| microcrystalline cellulose (Avicel PH-100) | 10 g |
| 1,2-propylene glycol | 100 g |
| flavor and color q.s. | |
| saccharin sodium | 0.5 g |
| dist. water q.s. to | 1000 ml |

In a stainless steel container Avicel is added to distilled water and 1,2-propylene glycol using an Ultra-Turrax mixer until a fine suspension is obtained. Then edulcorant, flavor and color are added, and finally 1-azaxanthone (mean particle size 10–30 μm) is slowly incorporated into the mixture.

What is claimed is:

1. A method of reducing fever in a mammal in need of said treatment, which comprises administering to said mamal, an atipyretic effective amount of 1-azaxanthone.

2. The method according to claim 1 wherein the 1-azaxanthone is in the form of a pharmaceutical composition which contains a pharmaceutically acceptable carrier.

3. A method of treating pain or inflammation in a mammal in need of said treatment which comprises administering to said mammal an analgesic or anti-inflammatory effective amount of 1-azaxanthone.

4. The method according to claim 3 wherein the 1-azaxanthone is in the form of a pharmaceutical composition which contains a pharmaceutically acceptable carrier.

5. A method of treating bronchoconstriction in mammals in need of said treatment which comprises administering to said mammal a bronchodilating effective amount of 1-azaxanthone.

6. The method according to claim 5 wherein the 1-azaxanthone is in the form of a pharmaceutical composition which contains a pharmaceutically acceptable carrier.

7. The method of claim 1, wherein the dose is within the range of 1 mg. per kilogram per day and 50 mg. per kilogram per day.

8. The method of claim 3, wherein the dose is within the range of 1 mg. per kilogram per day and 50 mg. per kilogram per day.

9. The method of claim 5, wherein the dose is within the range of 1 mg. per kilogram per day and 50 mg. per kilogram per day.

* * * * *